(12) United States Patent
Baek et al.

(10) Patent No.: US 8,772,534 B2
(45) Date of Patent: Jul. 8, 2014

(54) METHOD OF RECOVERING (METH) ACRYLIC ACID ESTER

(75) Inventors: Se-Won Baek, Daejeon (KR);
Hyun-Kyu Kim, Daejeon (KR);
Jun-Seok Ko, Daejeon (KR);
Kyoung-Su Ha, Anyang-si (KR);
Sung-Koo Park, Daejeon (KR);
Dong-Hyun Woo, Daejeon (KR)

(73) Assignee: LG Chem, Ltd., Seoul (KR)

( * ) Notice: Subject to any disclaimer, the term of this patent is extended or adjusted under 35 U.S.C. 154(b) by 642 days.

(21) Appl. No.: 13/055,425

(22) PCT Filed: Nov. 19, 2009

(86) PCT No.: PCT/KR2009/006835
§ 371 (c)(1),
(2), (4) Date: May 20, 2011

(87) PCT Pub. No.: WO2010/058983
PCT Pub. Date: May 27, 2010

(65) Prior Publication Data
US 2011/0230675 A1    Sep. 22, 2011

(30) Foreign Application Priority Data
Nov. 19, 2008  (KR) .................. 10-2008-0115393

(51) Int. Cl.
*C07C 69/54*        (2006.01)
*C07C 67/48*        (2006.01)

(52) U.S. Cl.
USPC ......................................... 560/218

(58) Field of Classification Search
None
See application file for complete search history.

(56) References Cited

U.S. PATENT DOCUMENTS

| | | |
|---|---|---|
| 5,910,603 A | 6/1999 | Aichinger et al. |
| 6,617,470 B1 | 9/2003 | Aichinger et al. |
| 2004/0225149 A1 | 11/2004 | Yada |
| 2004/0267045 A1 | 12/2004 | Yada et al. |
| 2006/0287550 A1 | 12/2006 | Otsuka et al. |

FOREIGN PATENT DOCUMENTS

| | | |
|---|---|---|
| CN | 1150586 A | 5/1997 |
| CN | 1326432 A | 12/2001 |
| CN | 1603297 A | 4/2005 |
| CN | 1608043 A | 4/2005 |
| CN | 1795168 A | 6/2006 |
| JP | 05-025086 | 2/1993 |
| JP | 2003-226671 | 8/2003 |

*Primary Examiner* — Yevegeny Valenrod
(74) *Attorney, Agent, or Firm* — McKenna, Long & Aldridge LLP

(57) ABSTRACT

The present invention provides a method of recovering a (meth)acrylic acid ester, which comprises the steps of: (a) carrying out an esterification reaction between an alcohol and (meth)acrylic acid in the presence of a catalyst to obtain a (meth)acrylic acid ester, wherein a byproduct is generated together with the (meth)acrylic acid ester; and (b) subjecting the byproduct generated in step (a) to a reaction with a catalyst and water in a reactor, wherein the water is fed into the reactor in order that water content exceeds 0 wt % but is 10 wt % or less in the reactor based on the total weight of reactants comprising the byproduct, the catalyst and the water, and thereby separating the (meth)acrylic acid, the alcohol and the (meth)acrylic acid ester contained in the byproduct from the byproduct to obtain the (meth)acrylic acid, the alcohol and the (meth)acrylic acid ester as a recovered product.

20 Claims, 2 Drawing Sheets

METHOD OF RECOVERING (METH) ACRYLIC ACID ESTER

TECHNICAL FIELD

The present invention relates to a method of recovering a (meth)acrylic acid ester wherein (meth)acrylic acid, an alcohol, and a (meth)acrylic acid ester are recovered from a byproduct generated in a process for preparing a (meth)acrylic acid ester. This application claims the benefit of PCT/KR2009/006835 filed on Nov. 19, 2009 and priority from Korean Patent Application No. 10-2008-0115393 filed on Nov. 19, 2008, both of which are incorporated herein by reference in their entirety.

BACKGROUND OF ART

Acrylic acid esters are prepared by an esterification reaction between acrylic acid and an alcohol. Inorganic acids, organic acids and solid acids are used as a catalyst for the esterification reaction. When one uses the inorganic acid catalyst (e.g., sulfuric acid) that is difficult to separate, the acid catalyst component in a product stream after the reaction is separated by adding a counter base such as sodium hydroxide and thus converting it into a salt.

Because such a treatment for separating the acid catalyst lays a burden on the process and the environment, it is preferable to adopt a process employing the organic acid or the solid acid which is easy to separate. In the case of the solid acid, a reaction entails a tendency of (mechanical, thermal and chemical) inactivation of the catalyst so that separation or a supplement of the catalyst is necessary and a relatively exacting process for separating the solids is required. The organic acids have an advantage that the recirculation of the catalyst is comparatively simple as they are easy to separate in the product stream.

In most processes for the esterification for acrylic acid esters, besides an effective product of the esterification reaction, various heavy byproducts such as the Michael adducts are generated from side reactions such as the Michael addition.

For example, in a process for preparing butyl acrylate, representative byproducts include butyl-b-butoxy propionate (BPB), b-butoxypropionic acid (BPA) and n-butyl diacrylate (BDA). Hereinafter, such byproducts are referred to as the "Michael Adducts." Although it is possible to minimize the occurrence of the side reactions by optimizing reaction conditions for the esterification, these byproducts are inevitably generated in almost all processes. To deal with such problems, prior arts proposed effective methods for decomposing and recovering these byproducts.

For these recovery methods to be successfully applied in the field, one should consider many aspects such as economic feasibility regarding the cost for the catalyst, corrosion of equipment and the disposal of waste steams after the final treatment.

Japanese Patent No. 1993-025086 suggested a process for decomposing the Michael adducts by adding an excessive amount of water with using sulfuric acid as a catalyst. However, the suggested process has drawbacks that it shows a low conversion rate of about 30% and consumes a lot of energy for the same reaction due to using an excessive amount of water.

U.S. Pat. No. 5,734,075 (issued in 1998) proposed a process of thermal cracking in the absence of catalyst on the byproducts from the esterification with the addition of a distillation residue stream originating from acrylic acid. It says that adding acrylic dimers or oligomers to the byproducts of the esterification process makes it possible to ensure the fluidity of the residue stream and the fouling phenomenon can be reduced as the process is operated in the absence of catalyst.

However, because this technique does not use any catalyst, the reactivity of the cracking is relatively low as compared with a process using a catalyst. Therefore, the conversion rate of about 80% at a considerably high temperature (280° C.) is required in order to obtain a high conversion rate, which renders the process economically unfavorable.

U.S. Pat. No. 5,910,603 (issued in 1999) described a process for catalytically decomposing the Michael adducts originating from the esterification of acrylic acid with using an organic or inorganic acid.

When using an organic acid catalyst, this process exhibits the conversion rate of about 80% at a temperature between 150° C. and 250° C. but it still needs a high temperature. Also, the process could not deal with a serious fouling problem in a residue stream after the cracking reaction and from the viewpoint of applying the process, leaching of the catalytic component remains unresolved.

In order to solve the fouling problem and the leaching of solids in the prior art, U.S. Pat. No. 6,617,470 (issued in 2003) adopts an alkylbenzene sulfonic acid with a longer chain than pTSA as an organic acid catalyst for use in the cracking process. As this process does not use pTSA, a fluidity of waste oils can be ensured. Disadvantageously, however, this process should additionally add and use a long chain alkylbenzene sulfonic acid that is relatively expensive and shows a low reactivity for a cracking process, or directly use it as a catalyst for the esterification reaction.

DETAILED DESCRIPTION OF THE INVENTION

Technical Objectives

An objective of the present invention is to provide a method of recovering (meth)acrylic acid ester wherein (meth)acrylic acid, an alcohol, and a (meth)acrylic acid ester are effectively recovered from a reaction byproduct generated from a process for preparing a (meth)acrylic acid ester, and at the same time the final waste oils after a decomposition reaction maintain their fluidity so as to improve a process efficiency and to allow a smooth application to the actual process.

Technical Solution

The present invention provides a method of recovering a (meth)acrylic acid ester, which comprises the steps of: (a) carrying out an esterification reaction between an alcohol and (meth)acrylic acid in the presence of a catalyst to obtain a (meth)acrylic acid ester, wherein a byproduct is generated together with the (meth)acrylic acid ester; and (b) subjecting the byproduct generated in step (a) to a reaction with a catalyst and water in a reactor, wherein the water is fed into the reactor in order that water content exceeds 0 wt % but is 10 wt % or less in the reactor during the reaction based on the total weight of reactants comprising the byproduct, the catalyst and the water, and thereby separating the (meth)acrylic acid, the alcohol and the (meth)acrylic acid ester contained in the byproduct from the byproduct to obtain the (meth)acrylic acid, the alcohol and the (meth)acrylic acid ester as a recovered product.

Advantageous Effect of the Invention

According to the present invention, the amount of waste oils from the esterification process for (meth)acrylic acid esters decreases and thus a production efficiency for the (meth) acrylic acid ester increases. Therefore, the process can lay a lesser burden on the environment and be smoothly operated in the field.

Also, it becomes easy for the (meth)acrylic acid, the alcohol, and the (meth)acrylic acid ester generated during a elimination reaction of the byproduct to be instantly eliminated out of the system and thus a high conversion rate can be achieved.

DESCRIPTION OF REFERENCE NUMERALS FOR THE MAIN PARTS OF THE DRAWINGS

Figure 1:
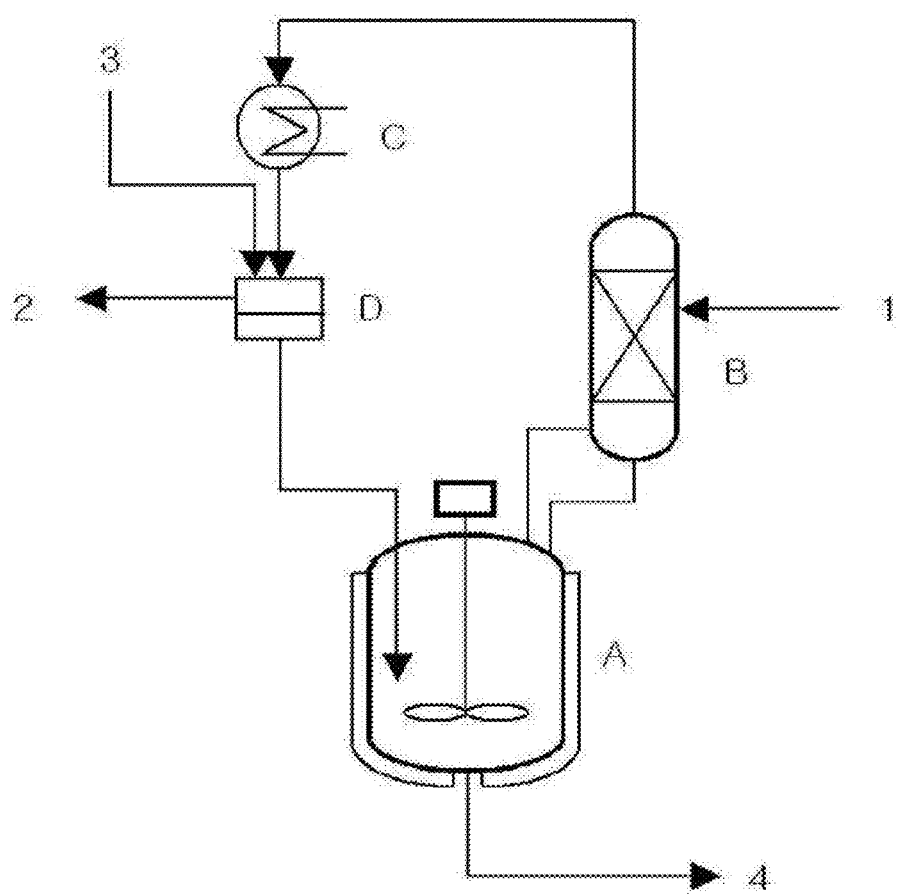
FIG. 1 is a view illustrating a process for recovering butyl acrylate in accordance with a first embodiment of the present invention.

A: a decomposition reactor
B: a recovery column
C: a condenser
D: a decanter
1: a supply line for a byproduct
2: a discharge line for a recovered product
3: a process water line
4: a discharge line for wastes

MODE FOR PRACTICING THE INVENTION

The method of recovering a (meth)acrylic acid ester in accordance with the present invention comprises the steps of: (a) carrying out an esterification reaction between an alcohol and (meth)acrylic acid in the presence of a catalyst to obtain a (meth)acrylic acid ester, wherein a byproduct is generated together with the (meth)acrylic acid ester; and (b) subjecting the byproduct generated in step (a) to a reaction with a catalyst and water in a reactor, wherein the water is fed into the reactor in order that water content exceeds 0 wt % but is 10 wt % or less in the reactor during the reaction based on the total weight of reactants comprising the byproduct, the catalyst and the water, and thereby separating the (meth)acrylic acid, the alcohol and the (meth)acrylic acid ester contained in the byproduct from the byproduct to obtain the (meth)acrylic acid, the alcohol and the (meth)acrylic acid ester as a recovered product.

The catalyst of step (a) can comprise at least one selected from the group consisting of one or more inorganic acid selected from sulfuric acid, phosphoric acid, and nitric acid; one or more organic acid selected from methanesulfonic acid and p-toluene sulfonic acid (pTSA); and one or more solid acid selected from zeolite and a polymer resin catalyst.

Step (a) can comprises the steps of: (a1) proceeding with the esterification reaction; and (a2) distilling products produced after the esterification reaction to separate them into the (meth) acrylic acid ester and the byproduct.

In this step, the esterification reaction proceeds in an esterification reactor and the distillation step is carried out in a distillation tower.

Specifically, the byproducts of step (b) can be supplied through two routes but the embodiments are not limited thereto.

When the distillation tower, a recovery column and a decomposition reactor (as an example of the reactor of step (b)) are connected through a supply line (see FIG. 1), the byproduct discharged from the lower side of the distillation tower (i.e., the byproduct separated in step (a2) of the distillation) can be supplied through the recovery column into the decomposition reactor.

In addition, when the distillation tower and the decomposition reactor is connected through the supply line without passing through the recovery column (see FIG. 2), the reaction byproducts discharged from the bottom of the distillation tower (i.e., the byproducts separated in step (a2) of the distillation) can be supplied into the decomposition reactor without passing through the recovery column.

The catalyst of step (b) can comprise at least one selected from the group consisting of one or more inorganic acid selected from sulfuric acid, phosphoric acid, and nitric acid; one or more organic acid selected from methanesulfonic acid and p-toluene sulfonic acid (pTSA); and one or more solid acid selected from zeolite and a polymer resin catalyst.

In step (b), the amount of the catalyst flowing in the reactor can be from 1 to 20 wt % based on the total weight of the reactants in the reactor. The amount of the catalyst flowing in the reactor can be preferably from 5 to 15 wt %, more preferably from 8 to 12 wt % based on the total weight of the reactants in the reactor.

If the byproduct fed into the reactor of step (b) contains the catalyst that is used in step (a), no additional catalyst for step (b) need be supplied since the catalyst for step (a) can act as the catalyst for step (b).

Also, if the byproduct contains no catalyst or such a trace amount of the catalyst for step (a) that no reaction can occur, a separate supply line for the catalyst can be provided to supply an additional catalyst that is to be used in step (b) into the reactor of step (b).

The water supplied into the reactor in step (b) can be fed into the reactor in such an amount that its content exceeds 0 wt % but is 10 wt % or less based on the total weight of the reactants (the byproduct+the catalyst+the water). Preferably, the water content in the reactor is maintained to exceed 0 wt % but to be 10 wt % or less while the water is fed into the reactor. Through this process, one can easily control a reaction temperature and a reaction pressure in the reactor. In addition, this process can give a higher conversion rate of the Michael adducts and an increased recovery rate thereof.

Preferably, the water supplied into the reactor in step (b) is fed in such an amount that its content exceeds 0 wt % but is 8 wt % or less, and more preferably ranges 3.5 to 5 wt %, based on the total weight of the reactants in the reactor.

If the water content in the reactor is 0 wt %, one cannot expect a rapid elimination of a product via hydrolysis or azeotropy and thus a conversion rate at a lower temperature cannot be raised sharply. If the water content in the reactor exceeds 10 wt %, the reaction temperature drops so much that the conversion rate decreases and control over a vaporization rate of water renders so difficult that a vapor product can contain an excessive amount of unreacted heavies and thus a recovery rate can decline.

Not only can the water take part in the decomposition reaction but also it can act as an azeotropic agent forming an azeotrope with the recovered product of step (b) recovered from the decomposition reaction of step (b) to lower the boiling point. In other words, the water forms an azeotrope with the recovered products after reaction to effectively remove them out of a reaction system and thereby can play a role in promoting the reaction. For example, the water forms an azeotrope with butanol or butyl acrylate recovered from the decomposition reaction to effectively remove it out of the reaction system and thereby can play a role in promoting the reaction.

In step (b), a flow rate of the water can be adjusted depending on the size of the reactor to be used. By way of example, the water can react for 0.5 to 10 hrs while being fed into the reactor with a flow rate of 0.3-3 g/min, but the present invention is not limited thereto. If a water supply rate is too high, the product to be recovered that is contained in the byproduct (e.g., BPB) can be taken away out of the reaction system. Preferably, the lower the supply rate, the less the spill of BPB.

The reactor of step (b) can be operated under the normal pressure (1,013 mmbar) or a reduced pressure (1-1,013 mmbar) at a reaction temperature of 80-180° C. for a residence time of 0.5 to 10 hrs. As long as the water content is maintained to exceed 0% but to be 10% or less, the reactor can be stably operated not in the high temperature and high pressure, but in the conditions as above. Herein, the term "residence time" refers to an average period of time in which the reactants (i.e., the byproduct, the water, and the catalyst) stay in the reactor while they are reacting together.

Most preferably, the reactor of step (b) is operated under a reduced pressure of 1-1,013 mmbar at a temperature of 100-150° C.

In step (b), the recovered product can be obtained in vapor state and such a recovered product of step (b) can be discharged from the upper side of the reactor and resupplied to step (a2) of the distillation, i.e. the distillation tower.

Alternatively, the recovered product of step (b) can be discharged from the upper side of the reactor and resupplied through a recovery column to step (a2) of the distillation, (i.e., the distillation tower). In addition, the recovered product of step (b) can be discharged from the upper side of the reactor and resupplied through the recovery column to step (a1) of the esterification reaction.

When the recovered product of step (b) is resupplied through the recovery column, the recovered product in vapor state that is discharged from the upper side of the reactor of step (b) and passes through the recovery column can be subject to (b1) a liquid state conversion step, wherein the recovered product in vapor state is condensed and undergoes a phase conversion to the recovered product in liquid state; and (b2) a water elimination step wherein the water contained in the recovered product from the liquid state conversion step is eliminated; and then it can be resupplied to step (a2) of the distillation or to step (a1) of the esterification step. Also, the water eliminated in the water elimination step can be resupplied to the reactor of step (b).

The liquid state conversion step can proceed in a condenser and the water elimination step can proceed in a decanter.

In this process, the water separated in the decanter where the water elimination step proceeds is discharged from the lower side of the decanter and resupplied to the reactor of step (b). The recovered product obtained after the water is eliminated in the decanter where the water elimination step proceeds can be discharged from the upper side of the decanter and resupplied to step (a1) of the esterification reaction or step (a2) of the distillation.

Specifically, in the decanter, the recovered products are separated into an organic layer and a water layer. The organic layer is the recovered product without water and the water layer is the water that was contained in the recovered product.

The water layer is discharged from the lower side of the decanter and used as water in the reactor of step (b). The recovered product obtained after the water is eliminated in the decanter can be resupplied to step (a2) of the distillation, or the esterification reactor.

In this process, the decanter can be additionally provided with a process water line through which the water can be supplemented as much as the water layer in the decanter decreases due to the reaction.

As described above, the recovered product of step (b) is recovered in vapor state and discharged from the upper side of the decomposition reactor and wastes generated other than the recovered product in step (b) can be discharged from the lower side of the reactor. As described above, when water is fed into the reactor, it is possible to ensure the fluidity of waste oils remaining after reaction.

Hereinafter, the present invention will be explained in detail with reference to the attached drawings.

First, specifically explained are the principles with regard to preparing and recovering acrylic acid esters in accordance with the present invention.

Acrylic acid esters (MA, EA, BA, and EHA) are obtained from a reaction between acrylic acid and an alcohol in the presence of an acid catalyst. Acrylic acid and an alcohol mostly react together to give an acrylic acid ester but some side reactions occur to convert them into the Michael adducts. The Michael adducts obtained as a byproduct generally have a higher boiling point than the acrylic acid ester so that they are obtained in the lower flow of the final distillation step.

When an organic acid is used as a catalyst for the esterification process, a mixture of the Michael adducts and the acid catalyst is obtained in the lower flow of the final distillation step.

As this lower flow is subject to the reaction again in the presence of an acid catalyst, the Michael adducts are inversely converted into an alcohol, acrylic acid and an acrylic acid ester and are recovered as a raw material such as acrylic acid and an alcohol and as a product of the acrylic acid ester. In this process, using a small amount of water as a reaction medium during a decomposition process in the presence of an acid catalyst can lower a decomposition temperature, assist the elimination of the product out of the system to increase a conversion rate, and secure a fluidity of the final waste oils to provide a flexibility for the process. In addition, the amount of the discharged wastes can be diminished and the process efficiency can be improved.

Hereinafter, a process for preparing butyl acrylate is exemplified for the shake of convenience in explanation, but the present invention is not limited thereto.

Representative examples of the Michael adducts generated in the preparation of butyl acrylate include butyl-b-butoxy propionate (BPB), b-butoxypropionic acid (BPA) and n-butyl diacrylate (BDA). A composition of a discharge stream obtained from the final distillation step can differ from process to process but it approximately comprises 0-5% of butanol, 0-10% of acrylic acid, 0-15% of butyl acrylate, 0-40% of BPB, 0-20% of BDA and 0-5% of BPA.

Figure 2:
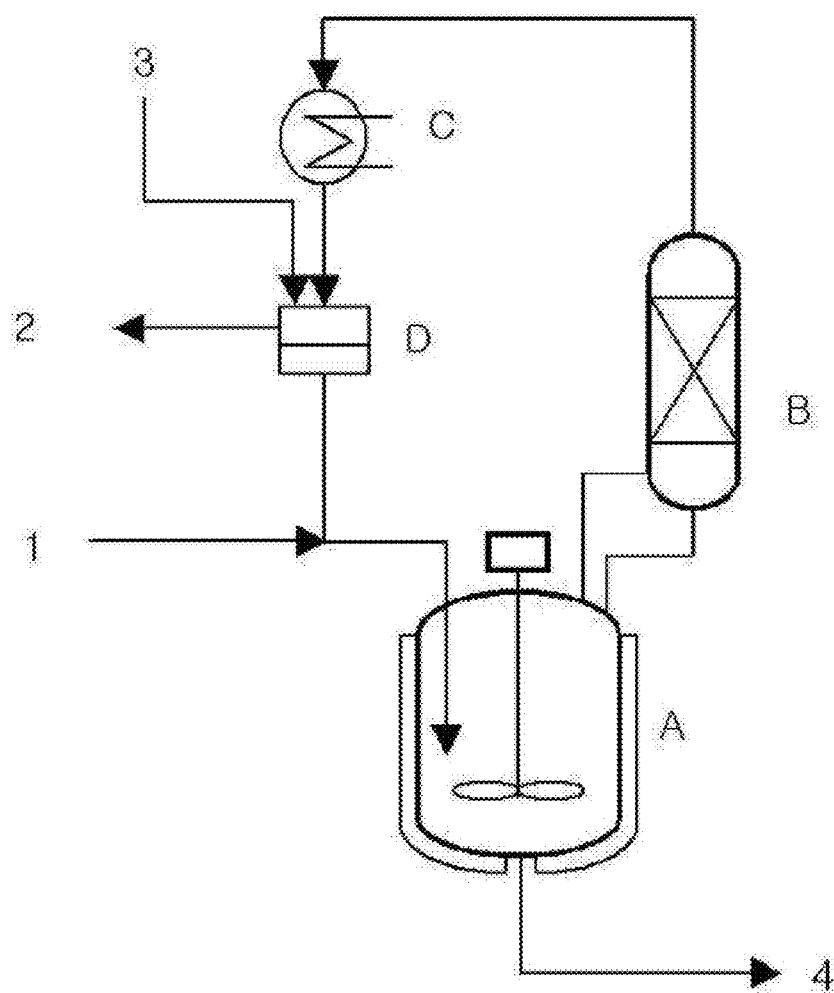
FIG. 2 is a view illustrating a process for recovering butyl acrylate in accordance with a second embodiment of the present invention.

FIGS. 1 and 2 are views illustrating a process for recovering butyl acrylate according to the present invention.

As shown in FIG. 1, after a process for preparing butyl acrylate is completed, a byproduct discharged from the bottom of a distillation tower (not shown) is fed into a decomposition reactor A via a supply line for a byproduct 1 and a recovery column B. As shown in FIG. 2, the byproduct discharged from the bottom of the distillation tower (not shown) can be directly fed into the decomposition reactor A via other supply line for the byproduct 1.

A small amount of water fed into the decomposition reactor A is the water discharged from the lower side of a decanter D and the water is supplemented through a process line 3 as much as the water layer in the decanter D decreases due to reaction.

The decomposition reactor A can be operated at a temperature of 80-180° C., preferably at a temperature of 100-150° C. With regard to a reaction pressure, in order to facilitate elimination of the product, the reactor can be operated under a reduced pressure that can be 1-1,013 mmbar taking into account the amount of the water as introduced into the decomposition reactor A. For a type of the reaction, both a batch reaction and a continuous reaction are available.

A catalyst introduced into the decomposition reactor A can enter through a separate line, but preferably is the same catalyst used in the process for preparing butyl acrylate and contained in the byproduct that is fed via the supply line for the byproduct 1.

As a catalyst, one can use an inorganic acid such as sulfuric acid, phosphoric acid, nitric acid, and the like; an organic acid such as methanesulfonic acid, p-toluene sulfonic acid (pTSA), and the like; and an solid acid such as zeolite and a polymer resin catalyst, but the types of the catalyst are not limited thereto.

Butanol, butyl acrylate, and acrylic acid, which are generated from the decomposition reaction in the decomposition reactor A, are discharged in vapor state together with water through the recovery column B, converted into liquid state in a condenser C, and introduced into the decanter D.

In this process, the recovery column B is preferably necessary, but in some cases, the recovered products (i.e., butanol, butyl acrylate, and acrylic acid) in vapor state discharged from the decomposition reactor A are introduced without passing through the recovery column into the esterification reactor where the esterification for obtaining butyl acrylate proceeds or the distillation tower where the distillation process for butyl acrylate proceeds.

In the decanter D, the products are separated into a water layer and an organic layer (i.e., the recovered product), and the organic layer (i.e., the recovered product) is then resupplied via a discharge line for a recovered product 2 to the esterification reactor (not shown) or the distillation tower. And, the water layer is resupplied to the decomposition reactor A.

After the byproduct stayed and reacted in the decomposition reactor A for a certain period of time, wastes generated therefrom end up being disposed through a discharge line for wastes 4. A fluidity of such a flow is of great importance in order for a process to be applied in the field and it depends on a degree of decomposition and properties of residues. When one uses an organic acid catalyst that is widely employed in a esterification process, a large amount of the catalyst is concentrated and flows in the discharge line for wastes 4 so that the precipitation tends to occur and highly viscous materials in the form of tar are increasingly discharged more as the degree of the reaction is getting higher.

Unlike the prior arts, the present invention resolves the foregoing problems by continuously feeding a small amount of water into the decomposition reactor A and it can be found that the byproduct shows a satisfactory reactivity for decomposition even at a relatively low temperature.

In the method of recovering a (meth) acrylic acid ester according to the present invention, after step (b), a conversion rate of the byproduct can be 60 to 99%, preferably 70 to 99%, and more preferably 70 to 95%, as defined by the following equation:

Conversion Rate=(a total amount of the byproduct as consumed through reaction/a total amount of the byproduct as introduced)×100.

In addition, a selectivity of the recovered product can be 45 to 85%, preferably 50 to 80%, and more preferably 55 to 75%, as defined by the following equation:

Selectivity=(a total amount of (meth)acrylic acid, an alcohol, and a (meth) acrylic acid ester as produced/a total amount of the byproduct as consumed through reaction)×100.

Also, a recovery rate of the recovered product can be 35 to 80%, preferably 45 to 75%, and more preferably 50 to 70%, as defined by the following equation:

Recovery rate=(a total amount of (meth)acrylic acid, an alcohol, and a (meth) acrylic acid ester as produced/a total amount of the byproduct as introduced)×100.

Hereinafter, the present invention will be explained more specifically with reference to the following examples.

In the examples and the comparative examples, the reactions were carried out in a reaction system. 300 g of the final distillation discharge with a composition of butanol (1%), acrylic acid (4%), butyl acrylate (2%), BPB (50%), BDA (30%), BPA (3%), and the miscellaneous components (a polymerization inhibitor and the heavies) (10%) was added with 30 g of pTSA as a catalyst and the reaction was carried out at a temperature of 120 to 150° C. under a reduced or normal pressure. Upon reaction, the water was introduced and circulated at a constant flow rate of 0.3 to 3 g/min by using a volumetric pump. After the reaction for 3 to 10 hours, an organic layer of gas condensates and a water layer were obtained and analyzed to compare the conversion rate, the selectivity, and the recovery rate of the byproduct, i.e., the Michael adducts, as defined by the following equations:

Conversion rate=(a total amount of the Michael adducts as consumed through reaction/a total amount of the Michael adducts as introduced)×100;

Selectivity=[a total amount of butanol, acrylic acid, and butyl acrylate as produced/a total amount of the Michael adducts as consumed through reaction]×100;

Recovery rate=[a total amount of butanol, acrylic acid, and butyl acrylate as produced/a total amount of the Michael adducts as introduced]×100;

Selectivity of the organic layer=[a total amount of butanol, acrylic acid, and butyl acrylate as recovered in the organic layer/a total amount of the Michael adducts as consumed through reaction]×100; and Recovery rate of the organic layer=[a total amount of butanol, acrylic acid, and butyl acrylate as recovered in the organic layer/a total amount of the Michael adducts as introduced]×100.

Example 1

The reaction was carried out at a temperature of 120° C. under a pressure of 400 mmbar for 3 hours with feeding water into the reactor at a circulation rate of 1.5 g/min. As a result of the reaction, 45% of 300 g of the input feed was recovered in the organic phase, the BPB composition of which was found to be 7.6%. The conversion rate, the selectivity, and the recovery rate as defined were calculated as follows: the conversion rate of the Michael adducts: 83.2%; the selectivity thereof: 60.5%; the recovery rate thereof: 50.3%.

Under the assumption that only the organic layer obtained after the reaction would be recovered, the selectivity of the organic layer and the recovery rate of the organic layer were calculated to be 51.6% and 43%, respectively.

In this case, a flow discharged from the bottom of the reactor was a single phase flow without any precipitation of a solid pTSA and the water content was found to be maintained at 5 wt %.

Example 2

The reaction was carried out at a temperature of 130° C. under a pressure of 1,013 mmbar for 3 hours with feeding water into the reactor at a circulation rate of 1.5 g/min. As a result of the reaction, 52% of 300 g of the input feed was recovered in the organic phase, the BPB composition of which was found to be 6.4%. The conversion rate, the selectivity, and the recovery rate as defined were calculated as follows: the conversion rate of the Michael adducts: 89.8%; the selectivity thereof: 61.3%; the recovery rate thereof: 55.0%.

Under the assumption that only the organic layer obtained after the reaction would be recovered, the selectivity of the organic layer and the recovery rate of the organic layer were calculated to be 55.6% and 49.9%, respectively.

In this case, a flow discharged from the bottom of the reactor was a single phase flow without any precipitation of a solid pTSA and the water content was found to be maintained at 4 wt %.

Example 3

The reaction was carried out at a temperature of 130° C. under a pressure of 1,013 mmbar for 3 hours with feeding water into the reactor at a circulation rate of 0.35 g/min. As a result of the reaction, 24% of 300 g of the input feed was recovered in the organic phase, the BPB composition of which was found to be 0.3%. The conversion rate, the selectivity, and the recovery rate as defined were calculated as follows: the conversion rate of the Michael adducts: 70.2%; the selectivity thereof: 58.0%; and the recovery rate thereof: 40.8%.

Under the assumption that only the organic layer obtained after the reaction would be recovered, the selectivity of the organic layer and the recovery rate of the organic layer were calculated to be 30.9% and 21.7%, respectively.

In this case, a flow discharged from the bottom of the reactor was a single phase flow without any precipitation of a solid pTSA and the water content was found to be maintained at 4 wt %.

Example 4

The reaction was carried out at a temperature of 150° C. under a pressure of 1,013 mmbar for 4 hours with feeding water into the reactor at a circulation rate of 0.35 g/min. As a result of the reaction, 44% of 300 g of the input feed was recovered in the organic phase, the BPB composition of which was found to be 0.1%. The conversion rate, the selectivity, and the recovery rate as defined were calculated as follows: the conversion rate of the Michael adducts: 84.8%; the selectivity thereof: 73.3%; and the recovery rate thereof: 62.2%.

Under the assumption that only the organic layer obtained after the reaction would be recovered, the selectivity of the organic layer and the recovery rate of the organic layer were calculated to be 56.1% and 47.6%, respectively.

In this case, a flow discharged from the bottom of the reactor was a single phase flow without any precipitation of a solid pTSA and the water content was found to be maintained at 3.5 wt %.

Example 5

The reaction was carried out at a temperature of 120° C. under a pressure of 400 mmbar for 10 hours with feeding water into the reactor at a circulation rate of 0.35 g/min. As a result of the reaction, 54% of 300 g of the input feed was recovered in the organic phase, the BPB composition of which was found to be 1%. The conversion rate, the selectivity, and the recovery rate as defined were calculated as follows: the conversion rate of the Michael adducts: 94.0%; the selectivity thereof: 68.4%; and the recovery rate thereof: 64.3%.

Under the assumption that only the organic layer obtained after the reaction would be recovered, the selectivity of the organic layer and the recovery rate of the organic layer were calculated to be 63.0% and 59.3%, respectively.

In this case, a flow discharged from the bottom of the reactor was a single phase flow without any precipitation of a solid pTSA and the water content was found to be maintained at 5 wt %.

Example 6

The reaction was carried out at a temperature of 100° C. under a pressure of 200 mmbar for 3 hours with feeding water into the reactor at a circulation rate of 1.5 g/min. As a result of the reaction, 30% of 300 g of the input feed was recovered in the organic phase, the BPB composition of which was found to be 6.7%. The conversion rate, the selectivity, and the recovery rate as defined were calculated as follows: the conversion rate of the Michael adducts: 62%; the selectivity thereof: 64%; and the recovery rate thereof: 39.7%.

Under the assumption that only the organic layer obtained after the reaction would be recovered, the selectivity of the organic layer and the recovery rate of the organic layer were calculated to be 40.5% and 25.1%, respectively.

In this case, a flow discharged from the bottom of the reactor was a single phase flow without any precipitation of a solid pTSA and the water content was found to be maintained at 5 wt %.

Comparative Example 1

Decomposition Reaction without Addition of Water (150° C., Normal Pressure)

Except that no water was added, the decomposition reaction was carried out in the same apparatus as that of Examples 1 to 5. As a result of the reaction performed at a temperature of 150° C. under a pressure of 1,013 mmbar for 5 hours, 3.5% of the input feed was recovered in the organic phase, and thus the recovery of an organic layer under normal pressure was found to be difficult. The BPB composition in the organic layer was 1.3%. The conversion rate, the selectivity, and the recovery rate as defined were calculated as follows: the conversion rate of the Michael adducts: 54.7%; the selectivity thereof: 48.7%; and the recovery rate thereof: 26.7%.

Comparative Example 2

Decomposition Reaction without Addition of Water (150° C., a Reduced Pressure)

Except that no water was added, the decomposition reaction was carried out in the same apparatus as that of Examples 1 to 5. As a result of the reaction performed at a temperature of 150° C. under a pressure of 50 mmbar for 3 hours, 49.6% of the input feed was recovered in the organic phase, the BPB composition of which was 10%. The conversion rate, the selectivity, and the recovery rate as defined were calculated as follows: the conversion rate of the Michael adducts: 47.6%; the selectivity thereof: 69.6%; and the recovery rate thereof: 33.1%.

Under the assumption that only the organic layer obtained after the reaction would be recovered, the selectivity of the organic layer and the recovery rate of the organic layer were calculated to be 65.8% and 31.3%, respectively.

In this process, a flow discharged from the bottom of the reactor showed a precipitation of a solid pTSA at normal temperature and brought about difficulties in pumping.

Comparative Example 3

Decomposition Reaction without Addition of Water
(180° C., Normal Pressure)

Except that no water was added, the decomposition reaction was carried out in the same apparatus as that of Examples 1 to 5. As a result of the reaction performed at a temperature of 180° C. under a pressure of 1,013 mmbar for 3 hours, 82.7% of the input feed was recovered in the organic phase, the BPB composition of which was 8%. The conversion rate, the selectivity, and the recovery rate as defined were calculated as follows: the conversion rate of the Michael adducts: 90.6%; the selectivity thereof: 91.7%; and the recovery rate thereof: 83%.

Under the assumption that only the organic layer obtained after the reaction would be recovered, the selectivity of the organic layer and the recovery rate of the organic layer were calculated to be 87.4% and 79.2%, respectively.

The conversion rate of the reaction and the recovery rate increased due to the high temperature. However, since the catalyst was precipitated and an excessive amount of tar component was formed in the bottom of the reactor and on the surface of the wall of the reactor, it was impossible to drain the lower flow and thus a continuous operation was practically impossible.

Comparative Example 4

With the Addition of Water Over 10%

The reaction was carried out at a temperature of 105° C. under a pressure of 1,013 mmbar for 4 hours with feeding water into the reactor at a circulation rate of 0.35 g/min. As a result of the reaction, 8% of 300 g of the input feed was recovered in the organic phase, the BPB composition of which was found to be 0.1%. The conversion rate, the selectivity, and the recovery rate as defined were calculated as follows: the conversion rate of the Michael adducts: 12.3%; the selectivity thereof: 26%; and the recovery rate thereof: 3.2%.

Under the assumption that only the organic layer obtained after the reaction would be recovered, the selectivity of the organic layer and the recovery rate of the organic layer were calculated to be 10.2% and 1.3%, respectively.

In this case, a flow discharged from the bottom of the reactor was in a single phase flow without any precipitation of a solid pTSA and the water content was found to be maintained at 12.4 wt %.

In accordance with the present invention, the present inventors could solve the problem associated with the prior art process of recovering the byproducts by continuously adding a small amount of water to the decomposition reactor and recirculating it. In the present invention, adding a small amount of water to a recovery reaction of the byproduct that is carried out in the decomposition reactor causes a hydrolysis reaction and thereby makes it possible to lower the reaction temperature. In addition, the added water acts as an azeotropic agent forming an azeotrope with the recovered product of step (b) that are recovered by the decomposition reaction of step (b) to lower the boiling point thereof. As a result of this, it becomes easy for the (meth) acrylic acid, the alcohols and the (meth) acrylic acid esters as produced to be instantly eliminated out of the system and thus a higher conversion rate can be achieved.

Also, when the water content is maintained to exceed 0% but to be 10% or less, the reactor can be stably operated under the above condition that is neither a high temperature nor a high pressure.

In addition, an increased solubility of the organic acid makes it possible to drain the wastes generated after the recovery reaction (i.e., the waste oils) in a single phase and thus it is possible to resolve the problems associated with flowing out the waste oils on the application of the process.

In particular, with using an organic acid with a good reactivity such as pTSA in the esterification reaction for obtaining (meth)acrylic acid esters and using the same catalyst in a recovery process, the decomposition and the recovery of the byproduct can be maximized.

Also, since the water continues to be supplied while circulating continuously, only a small amount of water can be consumed by reaction and supplied additionally.

The invention claimed is:

1. A method of recovering a (meth)acrylic acid ester, which comprises the steps of:
   (a) carrying out an esterification reaction between an alcohol and (meth)acrylic acid in the presence of a catalyst to obtain a (meth)acrylic acid ester, wherein a byproduct is generated together with the (meth)acrylic acid ester; and
   (b) subjecting the byproduct generated in step (a) to a reaction with a catalyst and water in a reactor, wherein the water is fed into the reactor in order that water content exceeds 0 wt % but is 10 wt % or less in the reactor during the reaction based on the total weight of reactants comprising the byproduct, the catalyst and the water, and thereby separating the (meth)acrylic acid, the alcohol and the (meth)acrylic acid ester contained in the byproduct from the byproduct to obtain the (meth) acrylic acid, the alcohol and the (meth)acrylic acid ester as a recovered product.

2. The method of recovering a (meth)acrylic acid ester according to claim 1, wherein step (a) comprises the steps of: (a1) proceeding with the esterification reaction; and (a2) distilling products produced after the esterification reaction to separate them into the (meth) acrylic acid ester and the byproduct.

3. The method of recovering a (meth)acrylic acid ester according to claim 2, wherein the byproduct separated in step (a2) of the distillation is supplied into the reactor of step (b).

4. The method of recovering a (meth)acrylic acid ester according to claim 2, wherein the byproduct separated in step (a2) of the distillation is supplied through a recovery column into the reactor of step (b).

5. The method of recovering a (meth)acrylic acid ester according to claim 2, wherein the recovered product is recovered in vapor state in step (b), and the recovered product of step (b) is discharged from the upper side of the reactor and then supplied to step (a2) of the distillation.

6. The method of recovering a (meth)acrylic acid ester according to claim 2, wherein the recovered product is recovered in vapor state in step (b), and the recovered product of step (b) is discharged from the upper side of the reactor and then supplied through a recovery column to step (a2) of the distillation.

7. The method of recovering a (meth)acrylic acid ester according to claim 6, wherein the recovered product in vapor state that is discharged from the upper side of the reactor of step (b) and passes through the recovery column is subject to a liquid state conversion step, wherein the recovered product in vapor state is condensed and undergoes a phase conversion to the recovered product in liquid state; and a water elimination step wherein the water contained in the recovered product from the liquid state conversion step is eliminated; and then it is supplied to step (a2) of the distillation.

8. The method of recovering a (meth)acrylic acid ester according to claim 7, wherein the water eliminated in the water elimination step is fed into the reactor of step (b).

9. The method of recovering a (meth)acrylic acid ester according to claim 7, wherein the liquid state conversion step proceeds in a condenser, and the water elimination step proceeds in a decanter.

10. The method of recovering a (meth)acrylic acid ester according to claim 9, wherein the water separated in the decanter where the water elimination step proceeds is discharged from the lower side of the decanter and supplied to the reactor of step (b), and the recovered product obtained after water is eliminated in the decanter where the water elimination step proceeds is discharged from the upper side of the reactor and supplied to step (a2) of the distillation.

11. The method of recovering a (meth)acrylic acid ester according to claim 9, wherein a process water line is connected to the decanter to supply a process water.

12. The method of recovering a (meth)acrylic acid ester according to claim 2, wherein the esterification reaction of step (a1) proceeds in an esterification reactor, and the recovered product is recovered in vapor state in step (b) and the recovered product of step (b) is discharged from the upper side of the reactor and supplied through a recovery column to step (a1) of the esterification reaction.

13. The method of recovering a (meth)acrylic acid ester according to claim 12, wherein the recovered product in vapor state that is discharged from the upper side of the reactor of step (b) and passes through the recovery column is subject to a liquid state conversion step, wherein the recovered product in vapor state is condensed and undergoes a phase conversion to the recovered product in liquid state; and a water elimination step wherein the water contained in the recovered product from the liquid state conversion step is eliminated; and then it is supplied to step (a1) of the esterification reaction.

14. The method of recovering a (meth)acrylic acid ester according to claim 13, wherein the water eliminated in the water elimination step is fed into the reactor of step (b).

15. The method of recovering a (meth)acrylic acid ester according to claim 13, wherein the liquid state conversion step proceeds in a condenser, and the water elimination step proceeds in a decanter.

16. The method of recovering a (meth)acrylic acid ester according to claim 1, wherein wastes generated other than the recovered product in step (b) are discharged from the lower side of the reactor of step (b).

17. The method of recovering a (meth)acrylic acid ester according to claim 1, wherein in the reactor of step (b), a reaction pressure is normal pressure or ranges from 1 to 1,013 mmbar and a reaction temperature is 80 to 180° C., and a residence time in the reactor for the reactants of step (b) comprising the byproduct, the water, and the catalyst is 0.5 to 10 hours.

18. The method of recovering a (meth)acrylic acid ester according to claim 1, wherein waste is introduced at a flow rate of 0.3 to 3 g/min in step (b).

19. The method of recovering a (meth)acrylic acid ester according to claim 1, wherein the catalyst of step (b) comprises at least one selected from the group consisting of one or more inorganic acid selected from sulfuric acid, phosphoric acid, and nitric acid; one or more organic acid selected from methanesulfonic acid and p-toluene sulfonic acid (pTSA); and one or more solid acid selected from zeolite and a polymer resin catalyst.

20. The method of recovering a (meth)acrylic acid ester according to claim 1, wherein after step (b), a conversion rate of the byproducts is 60 to 99%, a selectivity of the recovered product is 45 to 85%, and a recovery rate of the recovered product is 35 to 80%, as determined by the following equations:

Conversion rate=(a total amount of the byproducts as consumed through reaction/a total amount of a byproduct as introduced)×100;

Selectivity=(a total amount of (meth)acrylic acid, an alcohol, and a (meth) acrylic acid ester as produced/a total amount of the byproduct as consumed through reaction)×100; and Recovery rate=(a total amount of (meth)acrylic acid, an alcohol, and a (meth) acrylic acid ester as produced/a total amount of the byproduct as introduced)×100.

\* \* \* \* \*